United States Patent
Dunham et al.

(10) Patent No.: US 12,329,637 B2
(45) Date of Patent: Jun. 17, 2025

(54) MITRAL VALVES WITH INTEGRATED CUTTING FEATURES

(71) Applicant: Cornell University, Ithaca, NY (US)

(72) Inventors: Simon Dunham, New York, NY (US); Bobak Mosadegh, New York, NY (US); James K. Min, Brooklyn, NY (US); Tracey Lustig, New York, NY (US)

(73) Assignee: Cornell University, Ithaca, NY (US)

( * ) Notice: Subject to any disclaimer, the term of this patent is extended or adjusted under 35 U.S.C. 154(b) by 926 days.

(21) Appl. No.: 16/982,407

(22) PCT Filed: Mar. 21, 2019

(86) PCT No.: PCT/US2019/023396
§ 371 (c)(1),
(2) Date: Sep. 18, 2020

(87) PCT Pub. No.: WO2019/183372
PCT Pub. Date: Sep. 26, 2019

(65) Prior Publication Data
US 2021/0068951 A1 Mar. 11, 2021

Related U.S. Application Data

(60) Provisional application No. 62/646,009, filed on Mar. 21, 2018.

(51) Int. Cl.
*A61F 2/24* (2006.01)
*A61B 18/00* (2006.01)
*A61B 18/02* (2006.01)
*A61B 18/14* (2006.01)

(52) U.S. Cl.
CPC .......... *A61F 2/2427* (2013.01); *A61F 2/2418* (2013.01); *A61B 2018/00369* (2013.01);
(Continued)

(58) Field of Classification Search
CPC .... A61F 2/2427; A61F 2/2418; A61F 2/2412; A61F 2220/0008; A61F 2220/0016;
(Continued)

(56) References Cited

U.S. PATENT DOCUMENTS 6,217,600 B1 * 4/2001 DiMatteo .............. A61F 2/0105
606/198
2004/0092858 A1 5/2004 Wilson et al.
(Continued)

OTHER PUBLICATIONS

International Search Report and Written Opinion in International Patent Application No. PCT/US2019/023396 dated Jul. 4, 2019.
(Continued)

*Primary Examiner* — Katherine H Schwiker
*Assistant Examiner* — Lauren Dubose
(74) *Attorney, Agent, or Firm* — Foley & Lardner LLP

(57) ABSTRACT

The present disclosure describes a replacement valve that can remove or lacerate the anterior mitral leaflet (or other portion of the heart) to reduce the obstruction of the left ventricular outflow tract (LVOT). The replacement valve can include integrated cutting features to lacerate a leaflet of a heart valve. For example, the cutting features can include blades or electrosurgical features that can cut the leaflets to reduce obstruction of the LVOT. As the cutting features are integrated components of the replacement valve, the laceration of the leaflet can follow implantation of the replacement valve and enables for clinical decisions to be made based on the degree of obstruction to the LVOT following the implantation procedure.

10 Claims, 6 Drawing Sheets

(52) U.S. Cl.
CPC ............. *A61B 2018/00601* (2013.01); *A61B 2018/0212* (2013.01); *A61B 18/1492* (2013.01); *A61F 2220/0008* (2013.01)

(58) Field of Classification Search
CPC ............. A61F 2002/8483; A61F 2/848; A61F 2250/0071; A61B 2018/00369; A61B 2018/00601; A61B 2018/1412; A61B 2018/1467; A61B 2018/1497; A61B 2018/1495; A61B 18/14; A61B 18/1492; A61B 18/08; A61B 18/10; A61B 2018/00577; A61B 2018/00791; A61B 2018/00214; A61B 2018/0212; A61B 2018/00273; A61L 2430/20
USPC ........................................................ 606/200
See application file for complete search history.

(56) References Cited

U.S. PATENT DOCUMENTS

| | | | |
|---|---|---|---|
| 2005/0075718 A1* | 4/2005 | Nguyen | ............... A61F 2/2418 623/2.18 |
| 2007/0156137 A1* | 7/2007 | Geisel | .................. A61B 18/14 606/49 |
| 2007/0239260 A1* | 10/2007 | Palanker | ................... A61F 2/82 623/1.15 |
| 2013/0310928 A1* | 11/2013 | Morriss | ................ A61F 2/2466 623/2.18 |
| 2014/0180391 A1* | 6/2014 | Dagan | ................. A61N 1/0558 623/1.15 |
| 2014/0188157 A1* | 7/2014 | Clark | ................... A61F 2/0105 29/428 |
| 2015/0173897 A1 | 6/2015 | Raanani et al. | |
| 2015/0351903 A1 | 12/2015 | Morriss et al. | |
| 2017/0035565 A1 | 2/2017 | Stacchino et al. | |

OTHER PUBLICATIONS

Khan, et al., "Intentional Laceration of the Anterior Mitral Valve Leaflet to Prevent Left Ventricular Outflow Tract Obstruction During Transcatheter Mitral Valve Replacement"; JACC: Cardiovascular Interventions, vol. 9 Nov. 1, 2016.

International Preliminary Report on Patentability on PCT PCT/US2019/023396 dated Oct. 1, 2020.

* cited by examiner

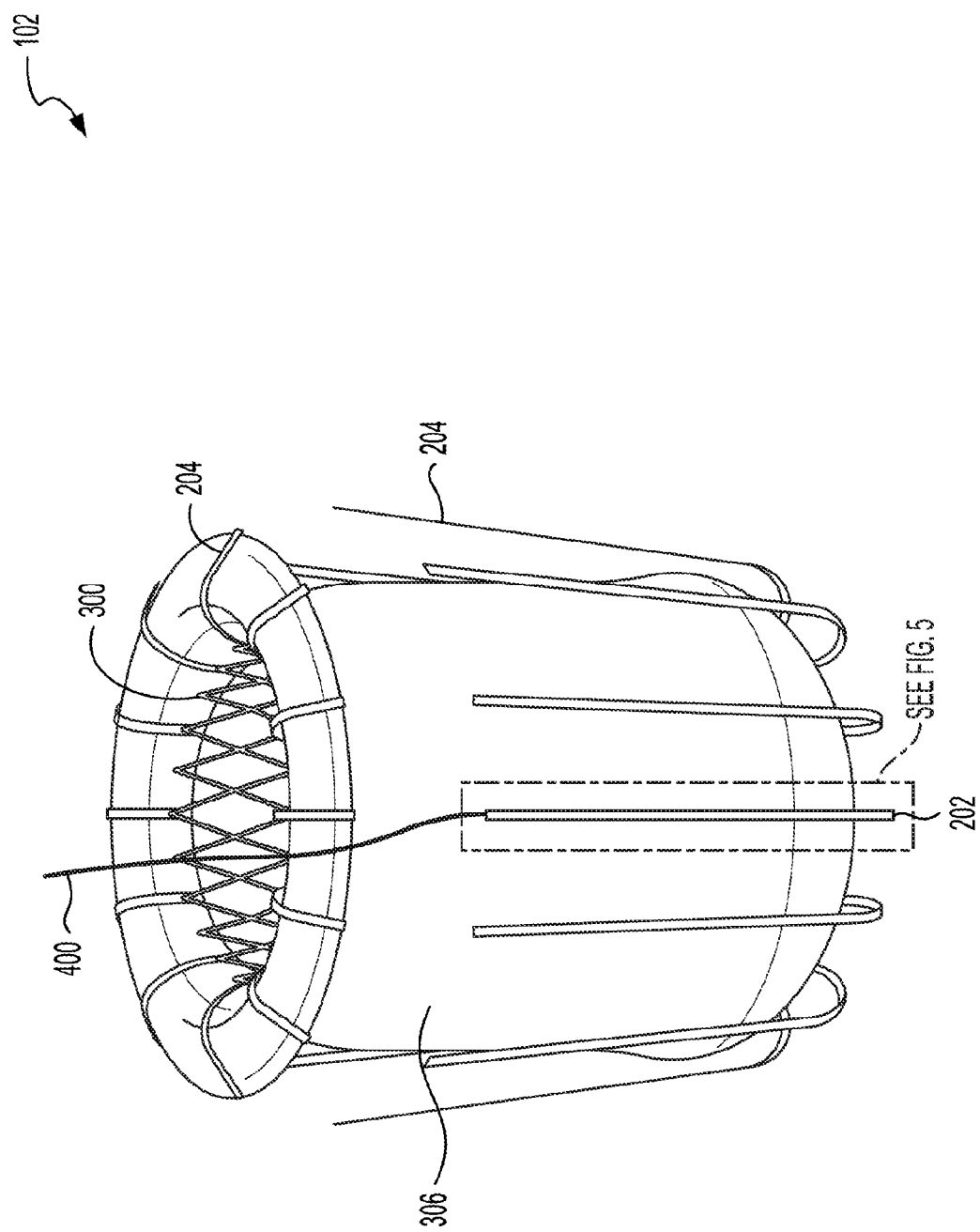

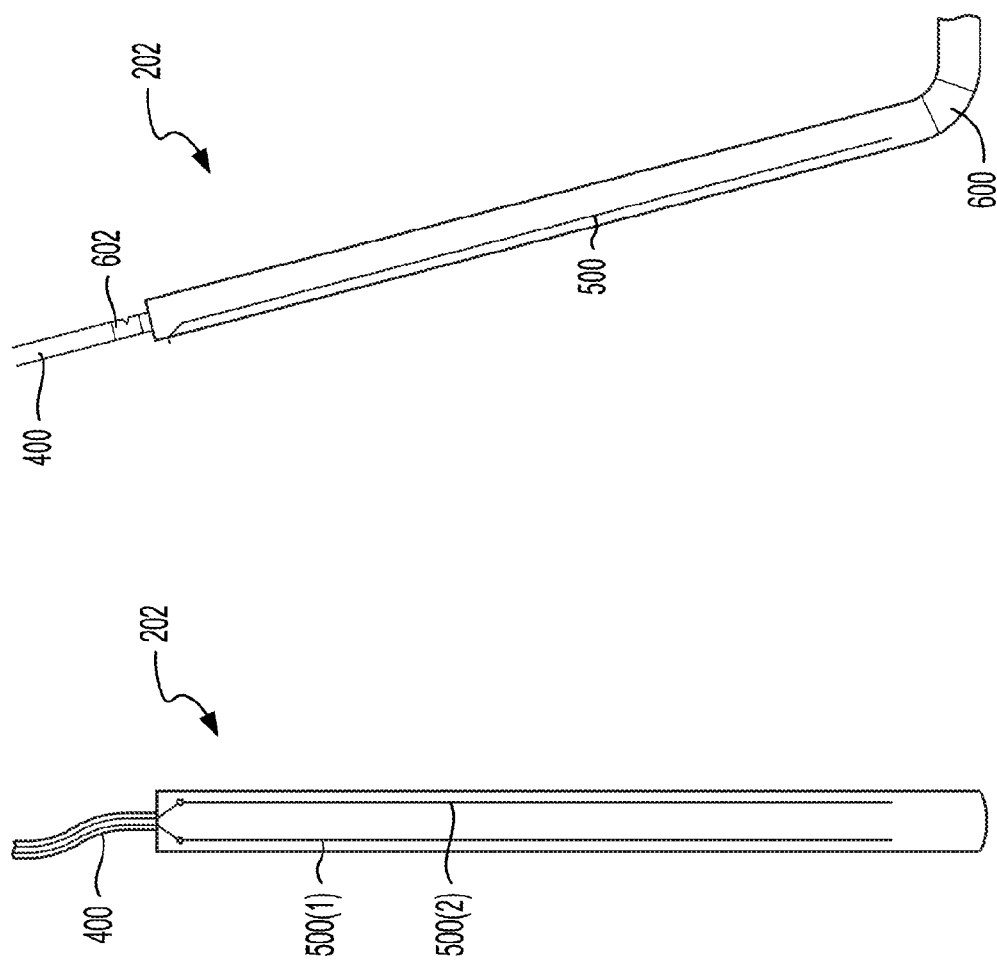

MITRAL VALVES WITH INTEGRATED CUTTING FEATURES

CROSS-REFERENCE TO RELATED APPLICATION

This application is a U.S. National Stage Application under 35 U.S.C. § 371 of International Patent Application No. PCT/US2019/023396, filed on Mar. 21, 2019, which claims priority to U.S. Provisional Patent Application No. 62/646,009 filed on Mar. 21, 2018, which are herein incorporated by reference in their entireties for all purposes.

BACKGROUND OF THE DISCLOSURE

Mitral regurgitation can occur when the native mitral valve is degraded and the leaflets of the mitral valve fail to fully close. The degraded leaflets can allow retrograde flow into the left atrium from the left ventricle. The mitral valve can be replaced with an artificial valve. The artificial valve can displace the anterior mitral leaflet into the left ventricular outflow tract (LVOT). Obstruction of the left ventricular outflow tract can reduce blood flow from the left ventricle to the aorta.

SUMMARY OF THE DISCLOSURE

The present disclosure describes a replacement valve that can remove or lacerate the anterior mitral leaflet (or other portion of the heart) to reduce the obstruction of the LVOT. The replacement valve can include integrated cutting features to lacerate a leaflet of a heart valve. For example, the cutting features can include blades or electrosurgical features that can cut the leaflets to reduce obstruction of the LVOT. As the cutting features are integrated components of the replacement valve, the laceration of the leaflet can follow implantation of the replacement valve and enables for clinical decisions to be made based on the degree of obstruction to the LVOT following the implantation procedure. For example, if the LVOT is not substantially obstructed, a physician may not engage the cutting features and the leaflet may not be cut. If the decision is made to lacerate the leaflet, the integration of the cutting features in to the replacement valve enables the leaflet to be lacerated without an additional procedure.

According to at least one aspect of the disclosure, a cardiac valve replacement device can include a stent body that can include a first end and a second end. The stent body can define a lumen. The device can include a prosthetic valve assembly coupled with an interior surface of the lumen. The device can include a first set of anchors extending the stent body to anchor the stent body to a target tissue location. The device can include at least one actuation arm extending from the stent body, the at least one actuation arm can include a cutting feature to cut a leaflet of a cardiac valve of a subject.

The cutting feature can include a blade extending from a face of the at least one actuation arm to cut the leaflet of the cardiac valve of the subject. The cutting feature can include at least one electrode to conduct a current to electrically cut the leaflet of the cardiac valve of the subject. The at least one actuation arm can include a second electrode to form a circuit with the first electrode through a portion of the leaflet of the cardiac valve of the subject.

The device can include a conductor coupled with the at least one actuation arm to deliver a current to the at least one actuation arm. The device can include a connector to couple the at least one actuation arm with the conductor. The connector can release the conductor from the at least one actuation arm. The connector can be a portion of the conductor and can include a breakpoint break and decouple the conductor from the at least one actuation arm when a predetermined force is applied to the conductor.

At least one actuation arm can include an insulator to electrically isolate the at least one actuation arm from the stent body. The connector delivers at least one of electrical energy, radio-frequency energy, kinetic energy, or cryogenic energy to the at least one actuation arm. The first set of anchors can extend from the first end of the stent body. The device can include a second set of anchors that extend from the second end of the stent body. The at least one actuation arm can be an anchor of the first set of anchors. The leaflet can be an anterior mitral valve leaflet.

According to at least one aspect of the disclosure, a method can include providing a replacement valve. The replacement valve can include a stent body that can include a first end and a second end. The stent body can define a lumen. The replacement valve can include a prosthetic valve assembly coupled with an interior surface of the lumen. The replacement valve can include a first set of anchors extending the stent body to anchor the stent body to a target tissue location. The replacement valve can include at least one actuation arm extending from the stent body. The at least one actuation arm can include a cutting feature to cut a leaflet of a cardiac valve of a subject. The method can include deploying the replacement valve through the cardiac valve of the subject. The method can include lacerating the leaflet of the cardiac valve of the subject with the at least one actuation arm including the cutting feature.

In some implementations, the cutting feature can include a blade extending from a face of the at least one actuation arm to cut the leaflet of the cardiac valve of the subject. In some implementations, the cutting feature can include at least one electrode to conduct a current to electrically cut the leaflet of the cardiac valve of the subject. The at least one actuation arm can include a second electrode to form a circuit with the first electrode through a portion of tissue. The method can include delivering a current, via a conductor coupled with the at least one actuation arm, to the at least one actuation arm. The current can have alternating frequency of between 100 kHz and 5 MHz.

The method can include applying a pulling force to a conductor coupled with the at least one actuation arm to release the conductor from the at least one actuation arm at a connector. The connector can be a portion of the conductor. The connector can include a breakpoint configured to break when a predetermined force is applied to the conductor. The at least one actuation arm can include an insulator to electrically isolate the at least one actuation arm from the stent body.

The method can include delivering at least one of electrical energy, radio-frequency energy, kinetic energy, or cryogenic energy to the at least one actuation arm. The first set of anchors extend from first end of the stent body. The replacement valve can include a second set of anchors extending from the second end of the stent body. The at least one actuation arm can be an anchor of the first set of anchors. The leaflet is an anterior mitral valve leaflet.

The foregoing general description and following description of the drawings and detailed description are exemplary and explanatory and are intended to provide further explanation of the invention as claimed. Other objects, advantages, and novel features will be readily apparent to those skilled in the art from the following brief description of the drawings and detailed description.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings:

FIG. 4 illustrates a perspective view of the replacement valve.

FIG. 5 illustrates a front view of the actuation arm of the replacement valve.

FIG. 6 illustrates a side view of the actuation arm of the replacement valve.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

The present disclosure describes a replacement heart valve. The replacement heart valve can include one or more integrated cutting features. The cutting features can either passively cut (e.g., with an integrated blade) or actively cut (e.g., through electrosurgery) the leaflet of the valve. Cutting the leaflet of the valve can increase the size of the constricted LVOT (termed the neo-LVOT) caused by the implantation of an artificial valve. As the cutting features are integrated into the replacement valve, the laceration of the leaflet can follow implantation of the replacement valve and enables clinical decisions to be made based on the size of the existing neo-LVOT following valve implantation. The replacement valve described herein enables the expansion of the neo-LVOT without the need of an additional procedure.

The replacement valve can include at least one cutting feature to remove, cut, or lacerate a leaflet of the heart. For example, the cutting feature can lacerate the anterior mitral leaflet. The cutting feature can be integrated into the replacement valve, affixed to the replacement valve, or integrated in a modular manner such that the cutting feature can be removed after use (or if not required). In some implementations, the laceration of the leaflet can be done unguided or utilizing visualization, via medical imaging modalities such as fluoroscopy, echocardiogram, or magnetic resonant imaging.

The cutting feature can be a sharp blade, tine, or other rigid feature affixed to the stent in a removable manner. In some implementations, the blade can be mechanically actuated by a user using, for example, pneumatic drive lines or wires to cause a cutting motion with the cutting feature to lacerate the leaflet.

The cutting feature can be an electrosurgical cutting feature. For example, a tine or anchor of the replacement valve 102 can be electrified to electrosurgically lacerate the leaflet. For example, the electrosurgical cutting feature can be activated with a radio-frequency alternating current to electrosurgically lacerate the leaflet.

Figure 1:
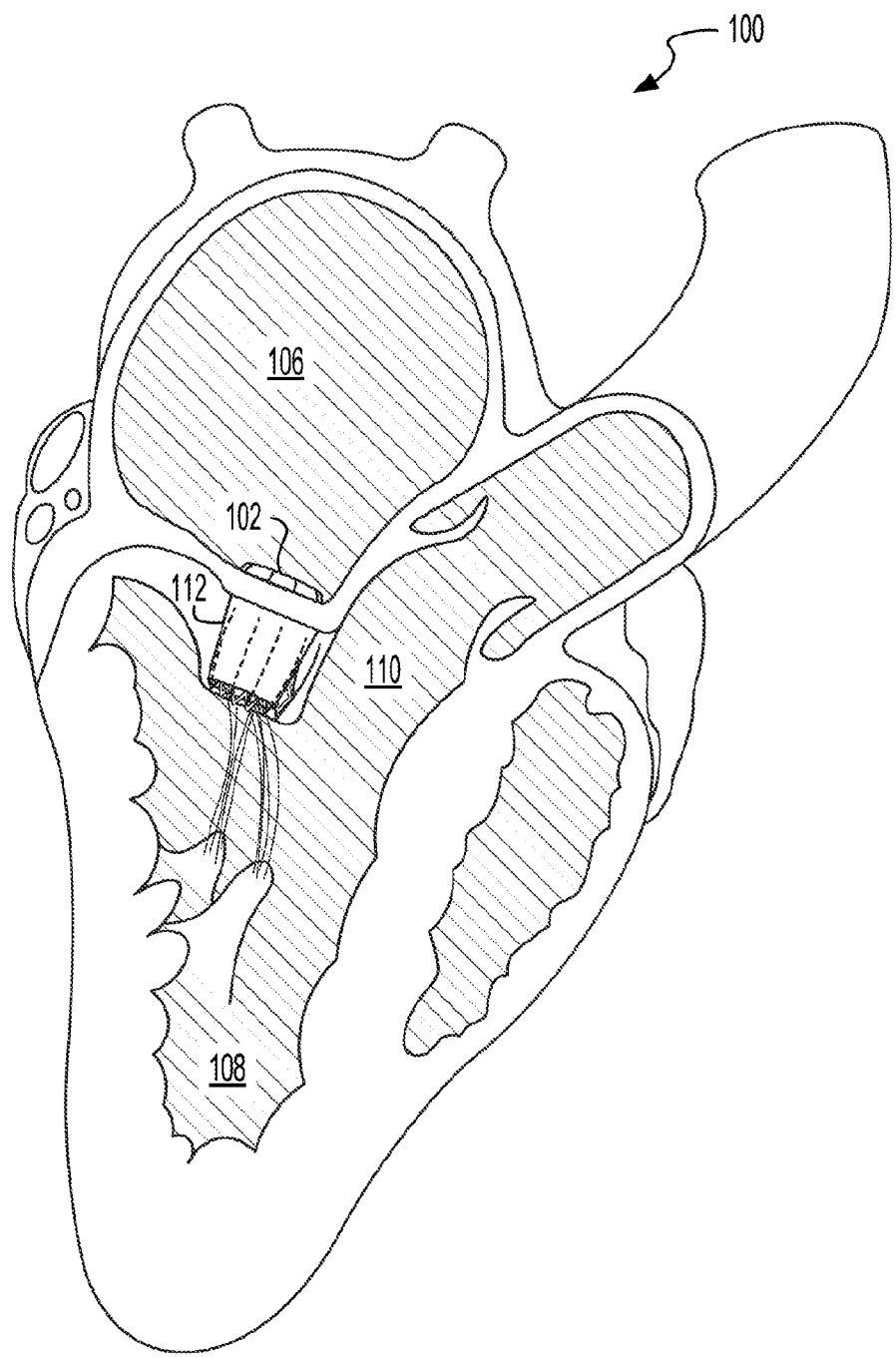
FIG. 1 illustrates a cross-sectional view of a heart of a subject implanted with the replacement valve.

FIG. 1 illustrates a cross-sectional view of a heart 100 of a subject. A replacement valve 102 is implanted into the heart 100. The replacement valve 102 can be a replacement valve for a heart valve, such as the mitral valve. For example, the replacement valve 102 can be implanted between the left atrium 106 and the left ventricle 108. The replacement valve 102 can be a one-way valve that controls blood flow from the left atrium 106 to the left ventricle 108 without allowing blood retrograde flow from the left ventricle 108 to the left atrium 106.

The replacement valve 102 can be an artificial vale to replace a subject's heart valve. The replacement valve 102 can replace the subject's mitral valve. The replacement valve 102 is described further in relation to FIGS. 2-7, among others. The replacement valve 102 can include one or more actuation arms that can include cutting features to cut or lacerate one or more leaflets of the subject's heart.

For example, when replacement valve is implanted into the heart 100, a mitral valve leaflet 112 (e.g., the anterior mitral valve leaflet) can be displaced toward the LVOT 110. The displacement of the leaflet 112 toward the LVOT 110 can obstruct fluid flow through the LVOT 110. As illustrated in FIG. 1, the replacement valve can include an actuation arm that includes one or more cutting features. The cutting features can lacerate the leaflet 112. Once lacerated, the leaflets 112 can withdraw medially and laterally around the body of the replacement valve. The withdrawal of the leaflets 112 withdraws the leaflets 112 from the LVOT 110 and reduces obstruction of the LVOT 110.

Figure 2:
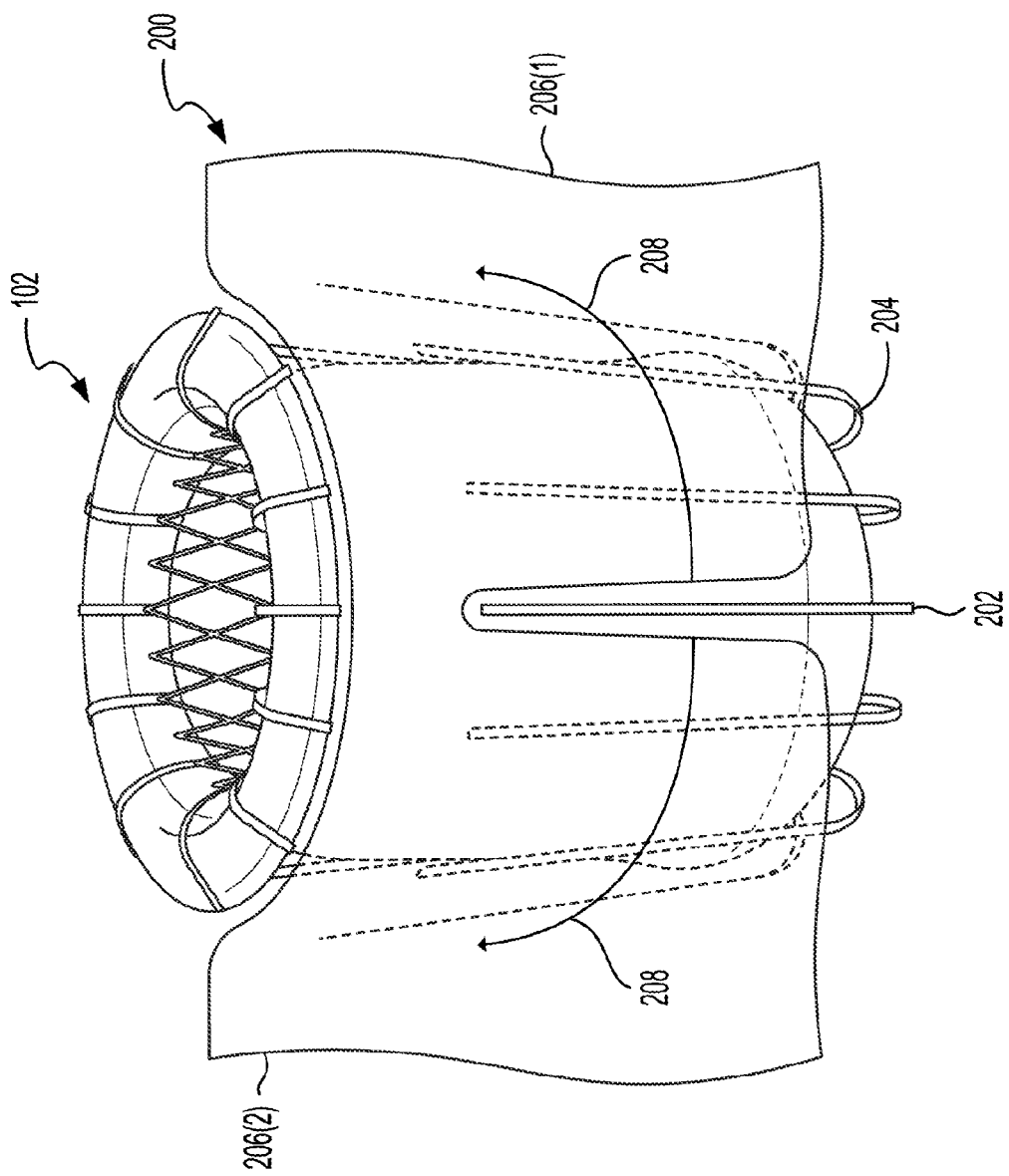
FIG. 2 illustrates a perspective view of the replacement valve behind a leaflet.

FIG. 2 illustrates a perspective view of the replacement valve 102 behind a leaflet 200. For example, the leaflet 200 can be the anterior mitral valve leaflet. The replacement valve 102 can include an actuation arm 202 that can include a cutting feature and the replacement valve 102 can include a plurality of anchors 204. In some implementations, the actuation arm 202 can be one of the anchors 204. For example, the actuation arm 202 can be an anchor 204 that includes a cutting feature.

FIG. 2 illustrates the leaflet 200 after laceration by the actuation arm 202 of the replacement valve 102. As illustrated in FIG. 2, the actuation arm 202 can lacerate, bisect, or otherwise transect the leaflet 200. For example, the replacement valve 102 can be implanted through the subject's mitral valve. The anchors 204 can anchor the replacement valve 102 in place. As described above, without transection, the leaflet 200 can displace into the LVOT 110 to form a neo-LVOT. The displacement of the leaflet 200 into the LVOT 110 can cause LVOT obstruction as the leaflet 200 (e.g., the anterior mitral valve leaflet) displaces toward the heart's septum.

As described further in relation to FIGS. 4-7, the actuation arm 202 can be activated to transect the leaflet 200. Activation of the actuation arm 202 transects the leaflet 200, as illustrated in FIG. 2. Once cut, the halfs 206(1) and 206(2) (generally referred to as halfs 206) displace around the body of the replacement valve 102 in the directions 208. The displaced halfs 206 of the leaflet 200 can reduce the obstruction of the LVOT 110 (increasing the size of the neo-LVOT). The tension of the leaflet 200, as applied by the heart's chordae tendineae, can displace the halfs 206 around the body of the replacement valve 102.

Figure 3:
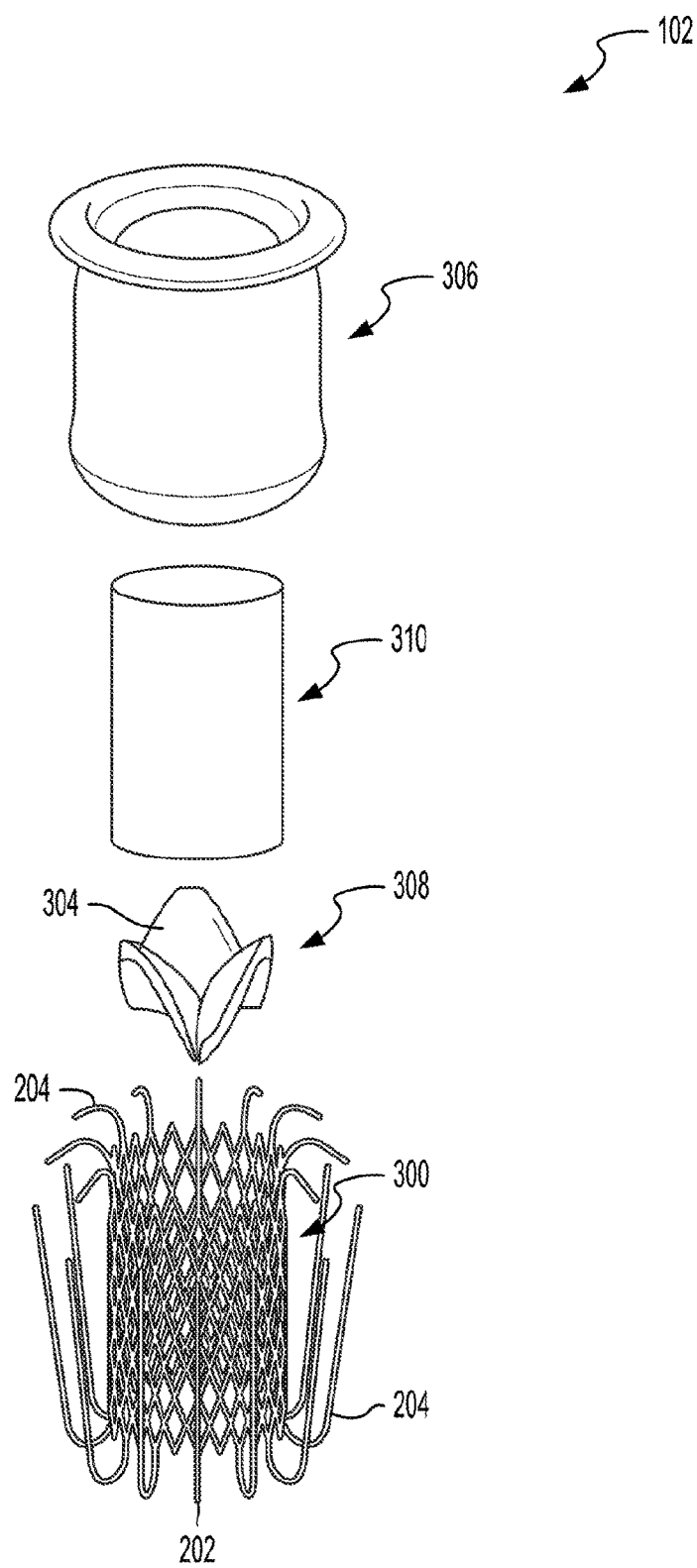
FIG. 3 illustrates an exploded view of the replacement valve.

FIGS. 3 and 4 illustrate the replacement valve 102. FIG. 3 illustrates an exploded view of the replacement valve 102. FIG. 4 illustrates a perspective view of the replacement valve 102. The replacement valve 102 can include a stent body 300, which can also be referred to as a body 300. A first set of anchors 204 can extend from a first end of the replacement valve 102. A second set of anchors 204 can extend from a second end of the replacement valve 102. The replacement valve 102 can include an actuation arm 202. In some implementations, the actuation arm 202 can be one of the anchors 204. The body 300 can define a lumen 302 that extends from the first end of the body 300 to the second end of the body 300. The replacement valve 102 can include a valve assembly 304 displaced within the lumen 302. The replacement valve 102 can include an enshroudment 306 that is displaced on an external face of the body 300 and an inner layer 310 that is displaced on an internal face of the body 300.

The replacement valve 102 can include a body 300. The body 300, anchors 204, and actuation arms 202 can include a shape memory alloy, such as nitinol. In some implementations, the replacement valve 102 can be deployed through a catheter. The replacement valve 102 and the body 300 can collapse to pass through the internal lumen of the catheter. After deployment from the catheter, the shape memory alloy can return to an original size and shape. The body 300, anchors 204, and actuation arms 202 can include titanium, stainless steel, cobalt-chromium, platinum chromium, or any combination thereof. The body 300 can be formed by braiding or knitting wires of, for example, nitinol. The body 300 can be formed by micro-machining or laser cutting a tube of nitinol, for example. The body 300 can have a length (e.g., height) between about 10 mm and about 100 mm, between about 20 mm and about 80 mm, or between about 30 mm and about 70 mm. When expanded, the body 300 can have an outer diameter of between about 5 mm and about 50 mm, between about 15 mm and about 50 mm, or between about 25 mm and about 50 mm. The lumen defined by the body 300 (or the inner diameter of the body 300) can be between about 4 mm and about 50 mm, between about 15 mm and about 50 mm, or between about 25 mm and about 49 mm.

The body 300 can include a first and second set of anchors 204. The first set of anchors 204 can extend from the first end (e.g., the inflow end) of the body 300. The second set of anchors 204 can extend from the second end (e.g., the outflow end) of the body 300. Each of the sets of anchors 204 can include between about 1 and about 10, between about 2 and about 10, or between about 4 and about 8 anchors 204. Each of the sets of anchors can include the same number of anchors 204 or a different number of anchors 204. The anchors 204 can be symmetrically spaced around the circumference of the body 300. The anchors 204 can be asymmetrically spaced around the circumference of the body 300. One set of anchors 204 can be symmetrically spaced around the circumference of the body 300 and the second set of anchors 204 can be asymmetrically spaced around the circumference of the body 300.

The first set of anchors 204 can extend from the first end (e.g., the inflow end) of the body 300. The first set of anchors 204 can form a lip. For example, the first set of anchors 204 can extend from the body at an angle between about 40° and about 90°, between about 45° and about 90°, between about 55° and about 90°, or between about 70° and about 90° with respect to the outer surface of the body 300. When the replacement valve 102 is implanted, the lip can seat against the anterior and posterior annulus, for example, of the subject's heart. The anchors 204 of the first set of anchors 204 can have a length between about 1 mm and about 30 mm, between about 5 mm and about 20 mm, or between about 5 mm and about 10 mm.

The second set of anchors 204 can extend from the second end (e.g., the output end) of the body 300. The second set of anchors 204 can extend from the second end of the body 300 and run along a length of the body 300. Each anchor 204 of the second set of anchors 204 can provide an outward force against the subject's native heart tissue to anchor the replacement valve 102 in place. In some implementations, one or more anchors 204 of the second set can include barbs or other anchoring mechanism to anchor the replacement valve 102 to the native heart tissue. In some implementations, the anchors 204 can serve as attachment points for the suturing of the replacement valve 102 to the native heart tissue. In some implementations, the anchors 204 of the second set of anchors 204 can have a length between about 10% and about 100%, between about 25% and about 90%, between about 50% and about 90%, or between about 75% and about 90% of the length of the body 300.

The replacement valve 102 can include a valve assembly 304. The valve assembly 304 can include a plurality of prosthetic leaflets 308. The valve assembly 304 can include 1, 2, 3, 4, or more prosthetic leaflets 308. The valve assembly 304 can be a one-way valve. For example, fluid flow from the input end toward the output end can drive the prosthetic leaflets 308 open and enable fluid (e.g., blood) to flow from, for example, the left atrium 106 to the left ventricle 108. Retrograde flow from the left ventricle 108 toward the left atrium 106 can drive the prosthetic leaflets 308 closed to substantially prevent flow from the left ventricle 108 to the left atrium 106. The prosthetic leaflets 308 can include tissue harvested from porcine, bovine, or homograft sources. The valve assembly 304 can be mechanical and the prosthetic leaflets 308 can include titanium, stainless steel, or a bio-compatible plastic.

The replacement valve 102 can include an inner layer 310. The inner layer 310 can line the inner face of the lumen 302. For example, the inner layer 310 can be a tube or cylinder that can be placed into the lumen 302 and coupled with the face of the lumen 302. The inner layer 310 can increase laminar flow through the lumen 302 when compared to when the wire of the body 300 is exposed to the fluid flow. The inner layer 310 can be a tube of DACRON™, expanded polytetrafluoroethylene (ePTFE), GORE-TEX™, or polyurethane.

The replacement valve 102 can include a enshroudment 306. The enshroudment 306 can cover the outer surface of the body 300 to reduce the formation of blood clots on or near the outer surface of the replacement valve 102. The enshroudment 306 can be the same material or a different material as the material of the inner layer 310. For example, the enshroudment 306 can include DACRON™, expanded polytetrafluoroethylene (ePTFE), GORE-TEX™, or polyurethane. The enshroudment 306 can have a thickness between about 0.1 mm and about 3 mm, between about 0.1 mm and about 2.5 mm, or between about 0.2 mm and about 2 mm.

The replacement valve 102 can include a conductor 400. The conductor 400 can couple with each of the actuation arms 202. The conductor 400 can enable the actuation of the respective actuation arms 202. For example, the conductor 400 can be a wire (or other electrical conductor) that electrically couples the actuation arm 202 (and the below-described electrodes) with a current generator to deliver current to the electrodes. In some implementations, the conductor 400 can include a lumen. For example, a coolant, such as argon gas, can be flowed through the lumen to the actuation arm 202 to cool the actuation arm 202 to enable the actuation arm 202 to cryogenically cut through the target tissue. The conductor 400 can be a pull or drive wire that enables the actuation arm 202 to be mechanically actuated. For example, the pulling of the conductor 400 can cause a mechanical motion (e.g., sawing) of the actuation arm 202 to cut the leaflet.

FIGS. 5 and 6 illustrate enlarged views of an example actuation arm 202. FIG. 5 illustrates a front view of the actuation arm 202. FIG. 6 illustrates a side view of the actuation arm 202. As described above, in some implementations, the actuation arm 202 can be a modified anchor 204. For example, the actuation arm 202 can have the same shape and dimensions as the anchors 204 and can also include one or more cutting features. The actuation arm 202 can be manufactured from the same material as the anchors 204 or a different material. For example, the anchor 204 may be manufactured from nitinol and the actuation arm 202 can be manufactured from or include an electrical insulator. The actuation arm 202 can include one or more cutting features to lacerate the leaflet 200. The cutting feature can lacerate the leaflet 200 with electrical energy, radio-frequency energy, cryogenic energy, or kinetic energy.

In some implementations, the actuation arm 202 can lacerate the actuation arm 202 with electrical energy (e.g., alternating current with a frequency less than about 100 kHz) or radio-frequency energy (e.g., alternating current with a frequency between about 100 kHz to 5 MHz). The actuation arm 202 can include at least one electrode 500 to deliver the electrical energy or radio-frequency energy to the tissue. The electrodes 500 can be an example cutting feature. The actuation arm 202 can include a first electrode 500(1) and a second electrode 500(2). The current can be delivered to the electrodes 500 via the conductor 400. The electrodes 500 can run along a length of the actuation arm 202. For example, the electrodes 500 can run along between about 10% and about 90%, between about 25% and about 90%, between about 50% and about 90%, or between about 75% and about 90% of the length of the actuation arm 202. Each of the electrodes 500 can be linear electrodes that run along a length of the actuation arm 202. For example, the electrodes 500 can be deposited as electrical traces along a length of the actuation arm 202. Each electrode 500 can be a series of discrete electrodes distributed along the length of the actuation arm 202. For example, the electrode 500 can include between about 2 and about 10 electrodes that are distribute along the length of the actuation arm 202 and coupled together by an insulated trace.

The electrodes 500 can be deposited on a face of the actuation arm 202 through a metal plating, sputtering, spin coating, or deposition process. For example, the metal of the electrodes 500 can be deposited onto the face of the actuation arm 202 through chemical vapor deposition. The electrodes 500 can include a conductive material, such as gold, platinum, silver, or copper. The actuation arm 202 can include a plurality of metal layers. For example, a plurality of traces can be deposited on a first, lower layer and the electrodes 500 can be deposited on a second, higher layer. The electrodes 500 can be coupled together by the traces in the first layer. In some implementations, the electrodes 500 and the traces can be deposited onto the same layer. For example, the electrodes 500 and traces can be deposited on a face of the actuation arm 202, the face of the actuation arm 202 can be encapsulated in an insulator (e.g., an epoxy), and portions of the insulator can be laser ablated to expose the electrodes 500 to the external environment.

The actuation arm 202 can operate in a bipolar configuration. In a bipolar configuration, the actuation arm 202 can include at least a first electrode 500 and a second electrode 500. When operated in the bipolar configuration, current can flow from the electrode 500(1) to the second electrode 500(2) through the external environment (e.g., the leaflet). For example, the electrode 500(1) can be coupled with a first pole of an alternating current (AC) generator. The electrode 500(2) can be coupled with the second pole of the AC generator. The AC generated by the AC generator can alternate between the electrode 500(1) and the electrode 500(2) via the external environment. In some implementations, the AC can alternate between a first electrode 500 on a first actuation arm 202 and a second electrode 500 on a second actuation arm 202.

The actuation arm 202 can be operated in a monopolar configuration. In a monopolar configuration, the actuation arm 202 can include one or more electrodes 500. For example, the entire distal portion of the actuation arm 202 can include a conductive metal and the conductive metal can be separated from the body 300 by an insulator 600. A grounding electrode can be coupled to a distant portion of the subject. When activated, the AC can alternate between the electrode 500 and the grounding electrode.

In some implementations, the actuation arm 202 can transect the target tissue with cryogenic energy. For example, the conductor 400 can include a lumen to deliver coolant (e.g., liquid nitrogen or argon gas) to the actuation arm 202. The actuation arm 202 can include one or more channels along the length of the actuation arm 202. The conductor 400 can be coupled with the channels such that the coolant cools the actuation arm 202. The cooled actuation arm 202 can freeze the cells of the target tissue to transect the target tissue.

In some implementations, the actuation arm 202 can transect the target tissue with kinetic energy. For example, the actuation arm 202 can include a cutting feature such as a blade, knife, or sharpened instrument that can lacerate the leaflet. A user can actuate the actuation arm 202 to force the actuation arm 202 through the target tissue.

The actuation arm 202 can include an insulator 600. The insulator 600 can electrically isolate the actuation arm 202 from the body 300. The insulator 600 can span the width of the actuation arm 202 and couple the actuation arm 202 with the body 300. The insulator 600 can include a poly(p-xylylene) polymer (e.g., Parylene™), a polyimide (e.g., Kapton (poly (4,4'-oxydiphenylene-pyromellitimide)), silicone, or other electrical insulator. In some implementations, the actuation arm 202 can include the same material as the insulator 600. For example, the actuation arm 202 can include a Kapton substrate onto which the electrodes 500 are deposited. When the electrodes 500 are energized, the insulator 600 (and insulation material of the actuation arm 202 in the above example) can electrically isolate the electrodes 500 from the body 300.

The replacement valve 102 can include a connector 602 that can couple the actuation arm 202 with the conductor 400. The connector 602 can be a breakaway connector that enables the conductor 400 to be decoupled from the actuation arm 202. In some implementations, the connector 602 can be a portion of the conductor 400 near the actuation arm 202 that can include a notch or score line that can serve as a breakaway point when a force is applied to the conductor 400. For example, the conductor 400 illustrated in FIG. 6 includes a connector 602 with a notch. After the replacement valve 102 is secured to the target tissue, the application of a force to the connector 602 by pulling the conductor 400 can cause the conductor 400 to break away from the actuation arm 202 at the connector 602. In some implementations, the connector 602 can be a coupler that is permanently coupled with one of the actuation arm 202 or the conductor 400 and reversibly coupled with the other. The coupler can apply a retaining force to the reversibly coupled one of the conductor 400 or actuation arm 202. When the pulling force applied exceeds the retaining force, the conductor 400 can decouple from the actuation arm 202 or the conductor 400. In some implementations, the connector 602 can include two portions that are coupled together by a suture or wire. The wire can have a relatively low tensile strength such that when a pulling force is applied to the conductor 400 the wire can break and enable the two portions of the connector 602 to separate.

In some implementations, the connector 602 can be at the base of the actuation arm 202. For example, the connector 602 can couple the actuation arm 202 with the body 300. In this example, the application of a pulling force on the conductor 400 can decouple the actuation arm 202 from the body 300 to enable the actuation arm 202 (and associated cutting feature) to be removed from the subject. For example, when the actuation arm 202 includes a sharpened tine to lacerate the leaflet, the actuation arm 202 can be separated from the body 300 at the connector 602 after the actuation arm 202 lacerates the leaflet. The actuation arm 202 can then be removed from the subject via the catheter used to implant the replacement valve 102.

Figure 7:
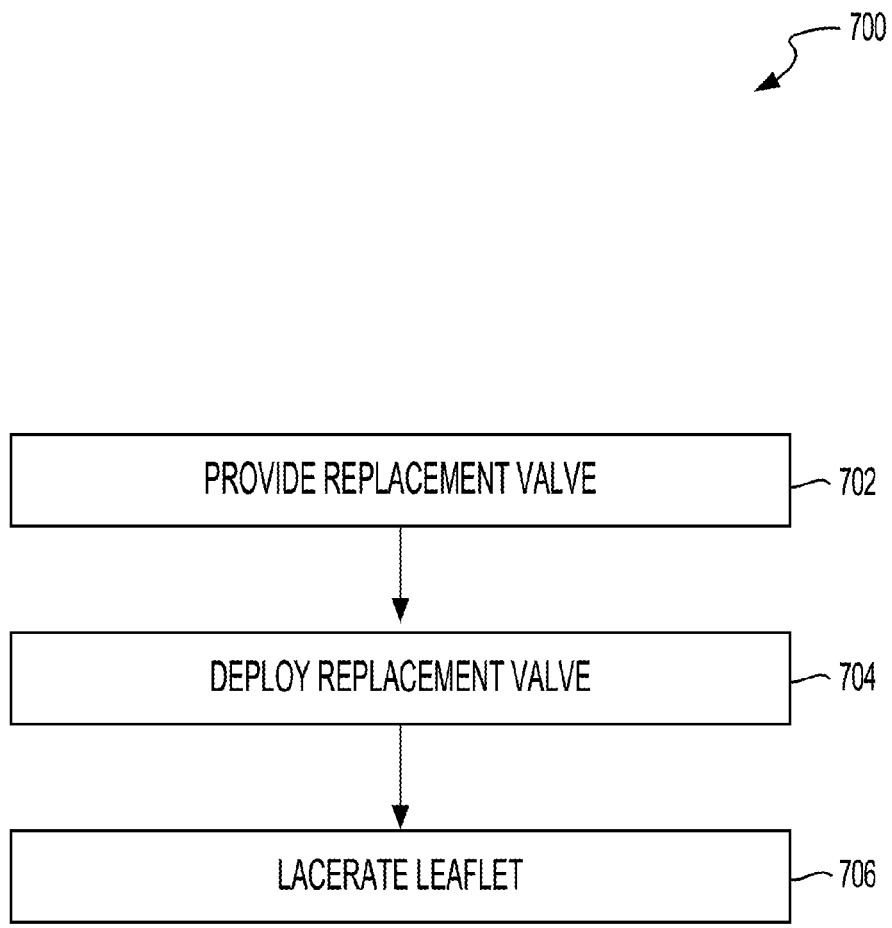
FIG. 7 illustrates an example method to implant the replacement valve in the heart of a subject.

FIG. 7 illustrates a block diagram of an example method 700 to implant a replacement valve. The method 700 can include providing a replacement valve (BLOCK 702). The method 700 can include deploying the replacement valve (BLOCK 704). The method 700 can include lacerating a leaflet (BLOCK 706).

As set forth above, the method 700 can include providing a replacement valve. Also referring to FIGS. 2-6, the replacement valve 102 can include a body 300. The body 300 can include a first end and a second end and can define a lumen. A first set of anchors 204 can extend from the first end and a second set of anchors 204 can extend from the second end. The replacement valve 102 can include a valve assembly 304 to allow fluid flow in substantially only one direction through the replacement valve 102. The valve assembly 304 can be coupled with an interior face of the lumen 302 of the body 300. The replacement valve 102 can include at least one actuation arm 202. In some implementations, the actuation arm 202 can be one of the anchors of the second set of anchors 204. The actuation arm 202 can be configured to cut or lacerate a leaflet of a cardiac valve of a subject. In some implementations, as described above, the replacement valve 102 can be manufactured from a memory shape alloy. The memory shape alloy enables the replacement valve 102 to be compressed to fit within the lumen of a catheter such that the replacement valve 102 can be implanted through a trans-catheter implantation procedure. When released from the catheter, the replacement valve 102 can expand to the original shape and size of the replacement valve 102.

The method 700 can include deploying the replacement valve (BLOCK 704). The replacement valve 102 can be deployed to a target site through trans-catheter implantation. For example, the replacement valve 102 can be included within the distal end of a delivery catheter. The delivery catheter can be between about 8 F and about 40 F, between about 15 F and 30 F, or between about 20 F and about 30 F. A physician can introduce the delivery catheter into the subject through a minimally invasive produce. For example, the physician can introduce the delivery catheter into the subject through a venous approach, such as the femoral vein, the subclavian vein, or the brachial vein. When a venous approach is used, a delivery catheter may be inserted into the left heart via a trans-septal puncture. The physician can introduce the delivery catheter into the subject through an arterial approach, such as the femoral artery, the brachial artery, or the carotid artery. When a venous approach is used, an inflow end of the replacement valve may be more distally positioned in the catheter than an outflow end. When an arterial approach is used, an outflow end of the replacement valve may be more distally positioned in the catheter than an inflow end. In some implementations, the delivery catheter can be introduced via a thoracotomy or a sternotomy. When a sternotomy or thoracotomy is used, a delivery catheter may be introduced via a transapical puncture or surgical cardiotomy. The location of the replacement valve 102 can be determined during the implantation of the replacement valve 102 with echocardiography, fluoroscopy, or by direct visualization.

The method 700 can include anchoring the replacement valve 102 to the native tissue of the subject. As described above, the replacement valve 102 can include one or more anchors 204. A first set of anchors 204 can form a lip of the replacement valve 102 that can mate, couple, or seal to the top face (e.g., left atrium face of the annulus) of the mitral valve being replaced or to the inner wall of the left atrium. The body 300 of the replacement valve 102 can extend through the native mitral valve tissue. The body 300 and the second set of anchors 204 can expand to come into contact with the native mitral valve tissue to anchor the replacement valve 102 in place. For example, prior to implantation, a CT scan can be performed to determine the size of the subject's mitral valve. Based on the size of the subject's natural mitral valve, a replacement valve 102 can be selected with a diameter that, when expanded, will cause the replacement valve 102 to press-fit into the passage between the left atrium and left ventricle. In some implementations, the replacement valve 102 can be coupled to the subject's heart. For example, the replacement valve 102 can be sutured to the wall of the subject's heart. In some implementations, the replacement valve 102 can include an internal balloon that can be inflated (with a gas, liquid, gel, epoxy, or other material) to expand the diameter of the body 300 to form a seal between the body 300 and the passage between the left atrium and left ventricle.

The method 700 can include lacerating a leaflet (BLOCK 706). As described herein, the replacement valve 102 can include at least one actuation arm 202. The actuation arm 202 can include one or more cutting features. The cutting features of the actuation arm 202 can be configured to lacerate or otherwise cut a leaflet (or other tissue) of the subject's heart. In some implementations, the actuation arm 202 can cut the leaflet to at least partially bisect the leaflet. The actuation arm 202 can bisect the leaflet to reduce obstruction to the left ventricle outflow tract. In some implementations, the actuation arm 202 can include a blade or knife that can cut the leaflet. In some implementations, the actuation arm 202 can include one or more electrodes to cut, with electrical energy, the leaflet. For example, and with reference to FIG. 5, an alternating current can alternate between an electrode 500(1) and an electrode 500(2). The alternating current between the electrodes 500 can generate a high heat that can ionize molecules, vaporize the water content of cells, and cut the tissue of the leaflet. The current can have a frequency in the radio frequency range. For example, the frequency of the current can be between about 100 kHz and about 5 MHz.

After implantation of the replacement valve 102 and laceration of the leaflet (if clinically needed), the actuation arm 202 or conductor 400 can be removed or decoupled from the replacement valve. In some implementations, the actuation arm 202 or the conductor 400 can include a score line that can serve as a breakpoint for the actuation arm 202 or the conductor 400. A physician can apply a force to the conductor 400 by pulling the conductor. The force can decouple (e.g., break) the actuation arm 202 or conductor 400 at the score line. The conductor 400 or actuation arm 202 can be retrieved through the catheter used to implant the replacement valve 102.

While operations are depicted in the drawings in a particular order, such operations are not required to be performed in the particular order shown or in sequential order, and all illustrated operations are not required to be performed. Actions described herein can be performed in a different order.

The separation of various system components does not require separation in all implementations, and the described program components can be included in a single hardware or software product.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements, and features discussed in connection with one implementation are not intended to be excluded from a similar role in other implementations.

The phraseology and terminology used herein is for the purpose of description and should not be regarded as limiting. The use of "including," "comprising," "having," "containing," "involving," "characterized by," "characterized in that," and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

As used herein, the term "about" and "substantially" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act, or element may include implementations where the act or element is based at least in part on any information, act, or element.

Any implementation disclosed herein may be combined with any other implementation or embodiment, and references to "an implementation," "some implementations," "one implementation," or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

The indefinite articles "a" and "an," as used herein in the specification and in the claims, unless clearly indicated to the contrary, should be understood to mean "at least one."

References to "or" may be construed as inclusive so that any terms described using "or" may indicate any of a single, more than one, and all of the described terms. For example, a reference to "at least one of 'A' and 'B'" can include only "A", only "B", as well as both "A" and "B." Such references used in conjunction with "comprising" or other open terminology can include additional items.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalence of the claims are embraced therein.

What is claimed:

1. A method, comprising:
    deploying a replacement valve through a cardiac valve of a subject, the replacement valve comprising:
        a stent body comprising a first end and a second end and defining a lumen;
        a prosthetic valve assembly coupled with an interior surface of the lumen;
        a first set of anchors extending from the stent body to anchor the stent body to a target tissue location; and
        at least one actuation arm extending from the stent body, the at least one actuation arm comprising a cutting feature to cut a portion of a heart;
    lacerating a leaflet of the cardiac valve of the subject with the cutting feature; and
    removing the cutting feature from the subject, wherein the removing the cutting feature comprises at least one of decoupling the actuation arm from the stent body or decoupling the cutting feature from the actuation arm.

2. The method of claim 1, wherein the cutting feature comprises at least a first electrode to conduct a current to electrically cut the leaflet of the cardiac valve of the subject, and wherein the at least one actuation arm comprises (i) a second electrode to form a circuit with the first electrode through a portion of tissue, and (ii) an insulator to electrically isolate the at least one actuation arm from the stent body.

3. The method of claim 1, further comprising delivering a current, via a conductor coupled with the at least one actuation arm, to the at least one actuation arm, wherein the current is an alternating frequency between 100 kHz and 5 MHz.

4. The method of claim 1, wherein the decoupling comprises applying a pulling force to a conductor coupled with the at least one actuation arm to release the conductor from the at least one actuation arm at a connector, wherein the connector is a portion of the conductor and comprises a breakpoint configured to break when a force is applied to the conductor.

5. The method of claim 1, further comprising delivering at least one of electrical energy, radio-frequency energy, or cryogenic energy to the at least one actuation arm.

6. The method of claim 1, wherein the first set of anchors extend from the first end of the stent body, wherein the replacement valve further comprises a second set of anchors extending from the second end of the stent body, and wherein the at least one actuation arm is an anchor of the first set of anchors.

7. The method of claim 1, wherein the leaflet is an anterior mitral valve leaflet.

8. The method of claim 1, wherein the cutting feature is an electrosurgical cutting feature, and wherein the leaflet is lacerated by activating a radio-frequency alternating current to electrosurgically cut the leaflet.

9. The method of claim 1, wherein the leaflet is cryogenically lacerated by cooling the at least one actuation arm.

10. The method of claim 1, wherein the decoupling comprises applying a pulling force to a first actuation arm of the at least one actuation arm to release the first actuation arm from the prosthetic valve assembly, wherein the first actuation arm comprises a score line configured to serve as a breakpoint for the first actuation arm.

* * * * *